United States Patent [19]

Blosser et al.

[11] Patent Number: 4,507,616
[45] Date of Patent: Mar. 26, 1985

[54] ROTATABLE SUPERCONDUCTING CYCLOTRON ADAPTED FOR MEDICAL USE

[75] Inventors: Henry G. Blosser, East Lansing; David A. Johnson, Williamston; Jack Riedel, East Lansing, all of Mich.; Richard J. Burleigh, Berkeley, Calif.

[73] Assignee: Board of Trustees operating Michigan State University, East Lansing, Mich.

[21] Appl. No.: 355,337

[22] Filed: Mar. 8, 1982

[51] Int. Cl.³ .............................................. H05H 13/00
[52] U.S. Cl. ...................................... 328/234; 313/62; 250/492.3
[58] Field of Search .................. 328/234; 313/62; 250/306, 307, 492.3, 400

[56] References Cited

U.S. PATENT DOCUMENTS

4,112,306  9/1978  Nunan ............................. 328/234 X

Primary Examiner—David K. Moore
Assistant Examiner—K. Wieder
Attorney, Agent, or Firm—Ian C. McLeod

[57] ABSTRACT

A superconducting cyclotron (10) rotatable on a support structure (11) in an arc of about 180° around a pivot axis (A—A) and particularly adapted for medical use is described. The rotatable support structure (13, 15) is balanced by being counterweighted (14) so as to allow rotation of the cyclotron and a beam (12), such as a subparticle (neutron) or atomic particle beam, from the cyclotron in the arc around a patient. Flexible hose (25) is moveably attached to the support structure for providing a liquified gas which is supercooled to near 0° K. to an inlet means (122) to a chamber (105) around superconducting coils (101, 102). The liquid (34) level in the cyclotron is maintained approximately half full so that rotation of the support structure and cyclotron through the 180° can be accomplished without spilling the liquid from the cyclotron. With the coils vertically oriented, each turn of the winding is approximately half immersed in liquid (34) and half exposed to cold gas and adequate cooling to maintain superconducting temperatures in the section of coil above the liquid level is provided by the combination of cold gas/vapor and by the conductive flow of heat along each turn of the winding from the half above the liquid to the half below.

17 Claims, 6 Drawing Figures

ROTATABLE SUPERCONDUCTING CYCLOTRON ADAPTED FOR MEDICAL USE

This invention was developed under National Science Foundation Contract PHY80-17605 and Department of Energy Contract DE-AC02-80ER10579. The U.S. Government as represented by the National Science Foundation has been granted a royalty-free license with right to sublicense for governmental purposes.

BACKGROUND OF THE INVENTION

1. Field of the Invention

The present invention relates to a superconducting cyclotron, particularly adapted for medical uses, which generates a beam of atomic particles or sub-particles, wherein the cyclotron and beam are rotatable in an arc around an object to be irradiated. In particular, the present invention relates to a cyclotron which is rotatable in an arc of about 180° without spilling a liquified gas at near 0° K. provided around magnetic pole coils for the cyclotron which renders them superconductive.

2. Prior Art

Various workers in the art have suggested that a relatively low power, e.g. about 25 to 75 MeV charged particle, superconducting, cyclotron which produces neutrons from the particles would be useful in medical treatment. Illustrative is an article by Hepburn et al, *Int. J. Radiation Oncology Biol Phys.* 3 387–391 (1977). The apparatus visualized as a concept by this publication includes a rotatable cyclotron with a support structure including a counterweight on a balance bar with a pivot pin at the fulcrum between the cyclotron and counterweight and with the pin rotatably attached to a mounting stand. The problem is that the design as conceived is not practical to construct. Liquid helium or other supercooled liquid gas presents a considerable handling problem when the cyclotron is rotated on such a support structure.

U.S. Pat. No. 3,868,522 shows a superconducting cyclotron with an air core rather than an iron core; however, the latter is preferred. Numerous superconducting cyclotron designs are known to the prior art.

OBJECTS

It is therefore an object of the present invention to provide a cyclotron with a practical support structure design. Further it is an object of the present invention to provide means for liquified gas (near 0° K.) connection to, confinement in and venting from the cyclotron which allows for ease of rotational movement of the cyclotron by the support structure. Further it is an object of the present invention to provide a support structure which is relatively simple and economical to construct. These and other objects will become increasingly apparent by reference to the following description and the drawings.

GENERAL DESCRIPTION

The present invention relates to a superconducting cyclotron apparatus including ion source means for providing a charged atomic particle to be spirally accelerated in the cyclotron with superconducting coils around iron magnetic poles and which can be cooled with a liquified gas to near 0° K., RF generator means connected to dees for accelerating the charged particles to generate a beam of particles or sub-particles from the spirally accelerated charged particles, the cyclotron including a support structure rotatable around a pivot axis for the cyclotron and balanced around the pivot axis by a counterweight on the support structure to thereby change the angle of the beam, wherein the beam can be directed towrds the axis in an arc defining a plane of rotation of the cyclotron by the support structure, the improvement in the support structure which comprises:

a balance bar with two ends including a counterweight at one end of the balance bar opposite a pivot axis and a cross bar member at the other end opposite the counterweight perpendicular to the balance bar and parallel to the pivot axis for supporting the cyclotron mounted on one end of the cross bar such that the beam can be generated in a plane perpendicular to and in the direction of the pivot axis;

pivot means supporting the balance bar at the pivot axis of the bar with the cyclotron and cross bar balancing the counterweight and with the pivot axis providing a fulcrum such that the balance bar is rotatable in an arc of about 180° in the plane perpendicular to the pivot axis;

drive means for rotating the balance bar in the arc as the beam is generated;

flexible hose attached at one end to the cross bar at an opposite end from the cyclotron for providing liquified gas cooled to near 0° K. through the hose to the cyclotron through an inlet conduit supported by the cross bar with an opposite end of the hose attached to a fixed base providing a mounting surface for the support structure, wherein as the cyclotron is moved in the arc the hose bends between the base and cross bar.

The present invention also relates to an improvement in a superconducting cyclotron apparatus which generates a beam of high velocity atomic particles or sub-particles around and above an object to be irradiated from spirally accelerated charged atomic particles which impinge upon a target to produce the beam, with a window and collimator on a first side of the cyclotron tangential to the spirally accelerated charged particles for defining the beam, including a support structure having a counterweight for the cyclotron and rotatable on a pivot axis between the cyclotron and counterweight for changing the angle of the beam in an arc of 180° or less defining a plane around the axis so that an object beneath the cyclotron can be irradiated around the axis the improvement in the cyclotron which comprises:

inlet means for supplying liquified gas to a vessel with a vent space from the vessel for releasing liquified gas which becomes a gas in the operation of the cyclotron adjacent the inlet means and with superconducting coils in the vessel vertically wound around spaced apart iron poles which can generate a magnetic field between the poles and which functions to produce the spirally accelerated particles with an oscillating electrical field, wherein the inlet means is mounted on a second side of the cyclotron opposite the window and collimator and wherein in use the liquified gas supplied by the inlet means fills up to approximately one-half of the vessel and partially covers each of the coils so that the coils are superconducting such that as the cyclotron is rotated in the arc, the liquified gas is below the inlet means and is thereby prevented from draining from the cyclotron through the vent space.

The present invention also relates to a method of using a superconducting cyclotron apparatus which generates a beam of high velocity particles or sub-particles from spirally accelerated charged particles which impinge upon a target to produce the beam with a window and collimator on a first side of the cyclotron tangential to the spirally accelerated charged particles for defining the beam, including a support structure for the cyclotron rotatable on a pivot axis for changing the angle of the beam in an arc of about 180° or less defining a plane around the axis so that an object beneath the cyclotron can be irradiated by the beam which comprises:

providing an object to be irradiated such that the beam irradiates the object as the cyclotron is rotated on the pivot axis;

supplying a liquified gas at near 0° K. in the cyclotron through an inlet means to a vessel containing vertically wound superconducting coils around iron poles for generating a magnetic field in the cyclotron which functions to produce the spirally accelerated charged particles with an oscillating electrical field, with a vent space from the vessel for releasing boil off liquified gas which becomes a gas during operation of the cyclotron adjacent the inlet means, wherein the inlet means is on a side of the cyclotron opposite the collimator and wherein the liquified gas fills up to approximately half of the vessel and partially covers each of the coils so that the coils are superconducting, such that when the cyclotron is rotated in the arc the liquified gas in the vessel remains below the inlet means and is thereby prevented from draining from the cyclotron through the vent space; and irradiating the object with the beam as the cyclotron is rotated in the arc.

SPECIFIC DESCRIPTION

The cyclotron is discussed first as to the support structure and then as to the cyclotron and finally as to the operation.

SUPPORT STRUCTURE FOR CYCLOTRON

A superconducting cyclotron 10 is shown in FIGS. 1 to 6 rotatably mounted on a support structure 11 which provides a means of irradiating a patient P with a neutron beam 12 with the cyclotron 10 in various positions. The support structure 11 includes a rotatable balance bar 13 with a counterweight 14 at one end of the balance bar 13 opposite a pivot axis A—A. A cross bar 15 is mounted on an end of the balance bar 13 opposite counterweight 14 and positioned perpendicular to the balance bar 13 and parallel to the pivot axis A—A. A hollow pivot pin 16 is mounted through balance bar 13 along axis A—A supported by roller bearings (not shown) in holders 17 such that the balance bar 13 is rotatable in an arc of about 180° in a plane perpendicular to the pivot axis A—A. The cyclotron 10 is mounted so as to be cantilevered on one end of the cross bar 15 such that atomic particles or subparticles (neutrons) 12 are generated in a plane perpendicular to and in the direction of the pivot axis A—A. Integral rounded reinforcement 15a provides support for the cross bar 15.

Figure 1:
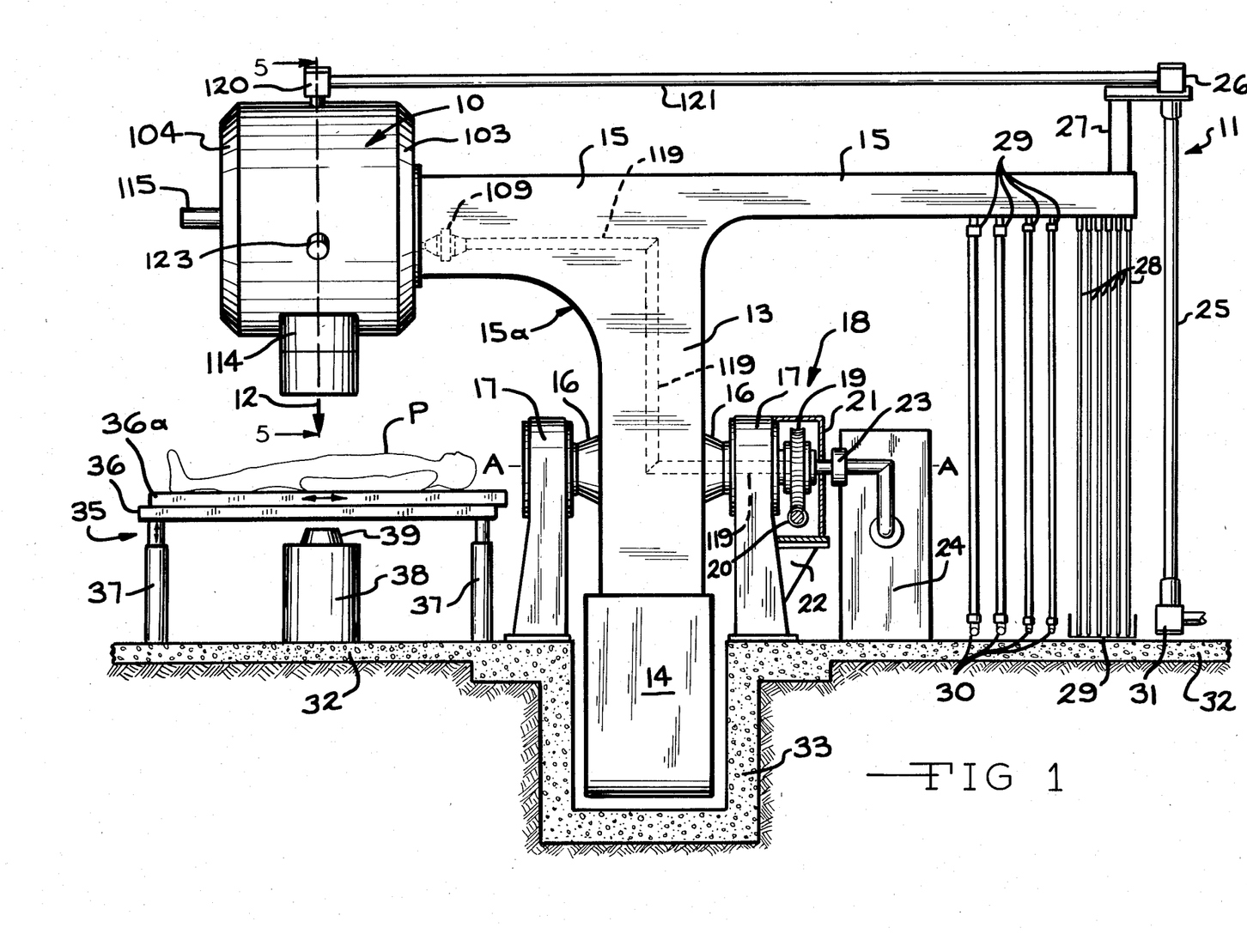
FIG. 1 is a front view of the superconducting cyclotron (10) and rotatable support structure (11) of the present invention, particularly illustrating a counterweighted (14) balance bar (13) and cross bar (15) supporting the cyclotron.

Drive means 18 for rotating balance bar 13 is provided, including a toothed circular gear 19 mounted on an extension of pivot pin 16 and mating worm gear 20 driven by a motor M, mounted in a housing 21 supported by gussets 22. RF coaxial transmission line 119 is routed along the rotation axis A—A through the side of the hollow pin 16 into the balance bar 13 and the cross bar 15 to a vacuum feed through insulator 109. The coaxial transmission line 119 is fed through a rotary RF joint 23 from an RF amplifier 24.

A quadruple walled flexible hose 25 is used, the center passage of which is used for supplying liquified gas, which is surrounded by an insulating vacuum annulus (not shown), which is in turn surrounded by an annular conduit which is used for the return of cold boil off gas from chamber 105 and which is in turn surrounded by an annulus (not shown) which is used for providing an insulating vacuum. The hose 25 is connected via a coupling 26 to conduit 122 leading to and conduit 121 leading from the cyclotron 10. Conduit 121 is mounted on cross bar 15 by means of a bracket 27. The flexible hose 25 is available from Eltek Corporation, Larchmont, N.Y. and allows for movement of the cross bar 15 and balance bar 13 in an arc as particularly illustrated in FIG. 3 for positions I, II and III. Similarly, flexible electrical cable 28 for coils 101 and 102 and ion source 110 supplies current. Flexible water cooling lines 29 for cooling ion source 110, target 111 and RF components 116, lead to and through (not shown) cross bar 15 to cyclotron 10. Opposite ends of cables 28, cooling water conduits 29 and liquified gas conduit 25 are rigidly connected through connectors 29, 30 and 31, respectively, to a mounting pad 32, preferably of concrete.

Figure 6:
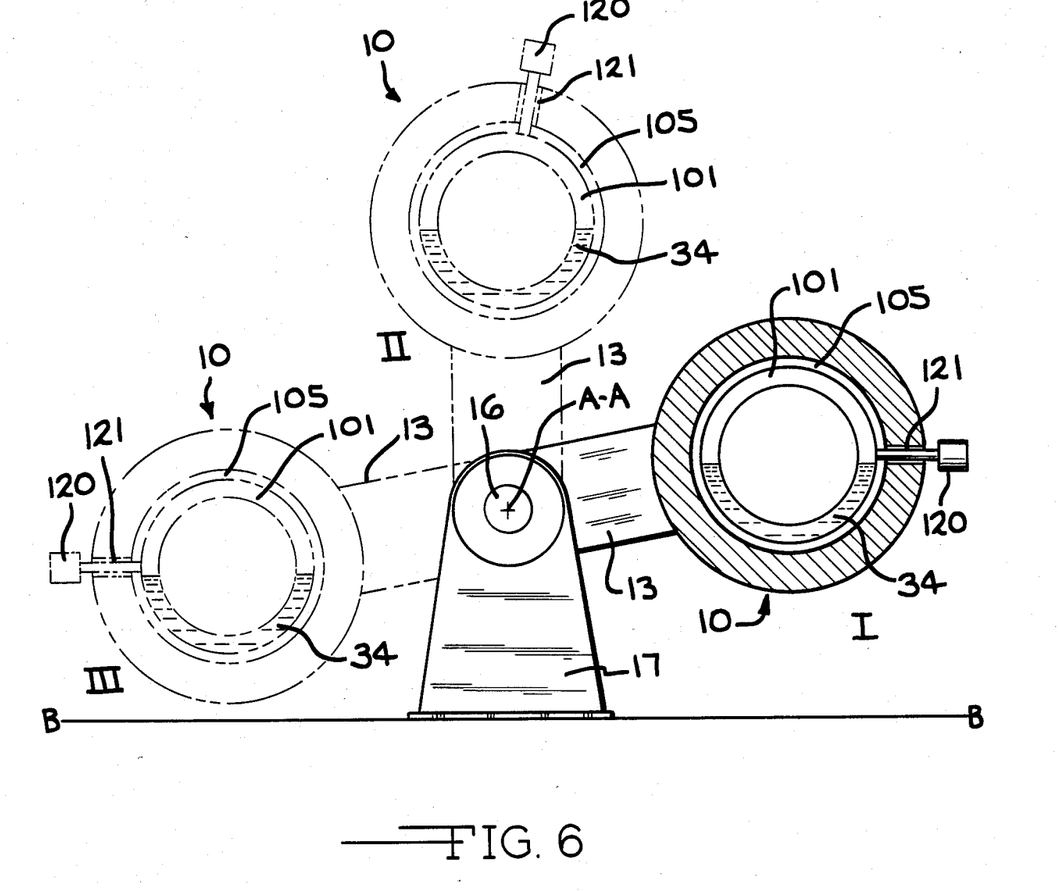
FIG. 6 is a right end view of the cyclotron and support structure of FIG. 1 showing a partial section of the vessel (105) filled with liquified gas (34) near 0° K. in various positions in a 180° arc.

The counterweight 14 is provided in a recess or well 33 in pad 32 so as to place the neutron producing target 111 approximately 1.5 meters from patient P and pad surface B—B. As shown in FIG. 6, the liquified gas levels 34 in the various positions I, II and III in a 180° arc about axis A—A never reach a level where liquid is released through vents 121 from the interior of the cyclotron. The helium vessel 105 is approximately half filled around coils 101 and 102 which by virtue of the orientation of these coils 101 and 102 is sufficient for cooling the coil conductor to a superconducting temperature.

Figure 2:
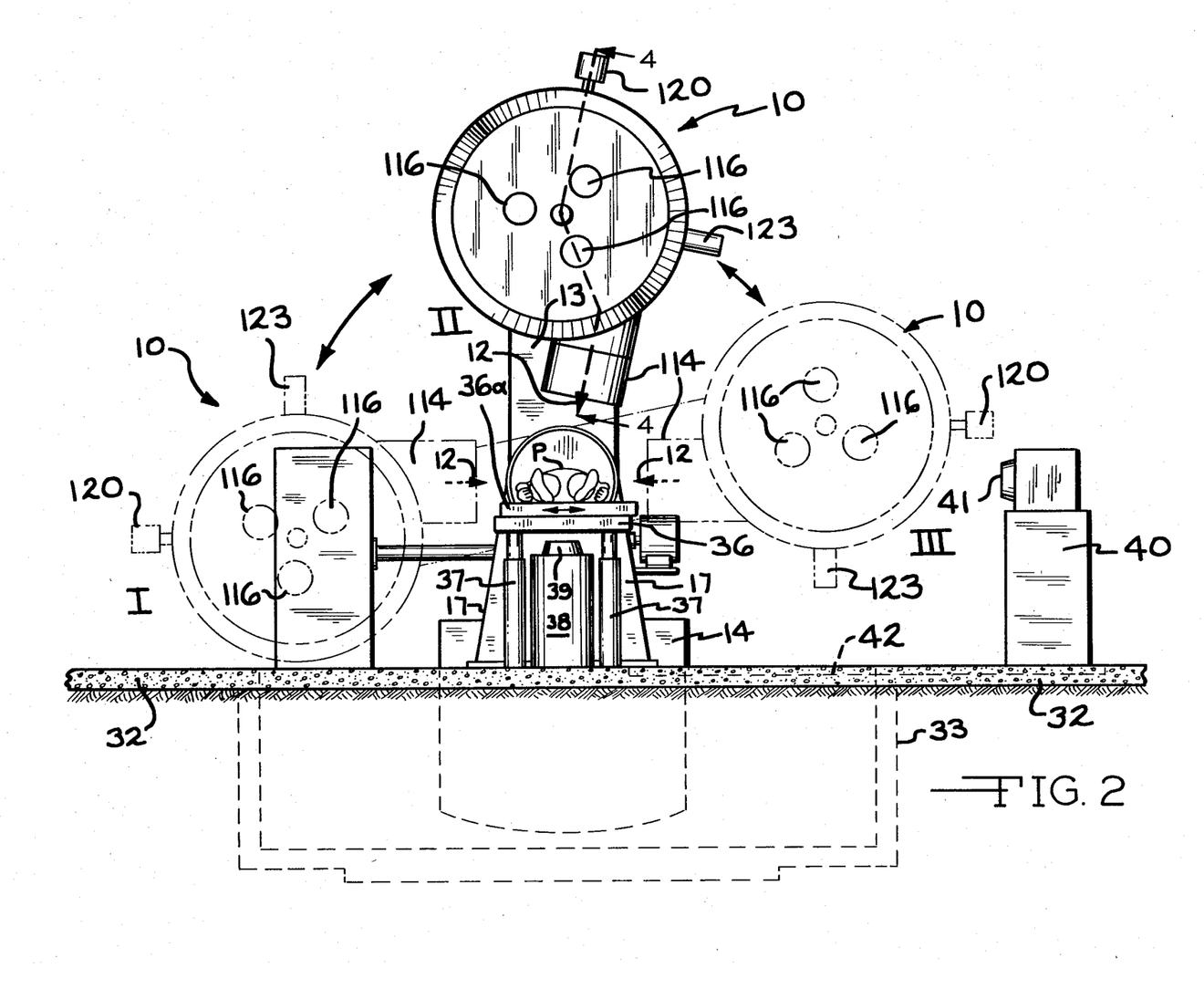
FIG. 2 is a left end view of the cyclotron and support structure of FIG. 1, particularly illustrating various positions of the cyclotron as a result of rotation of the balance bar.
Figure 3:
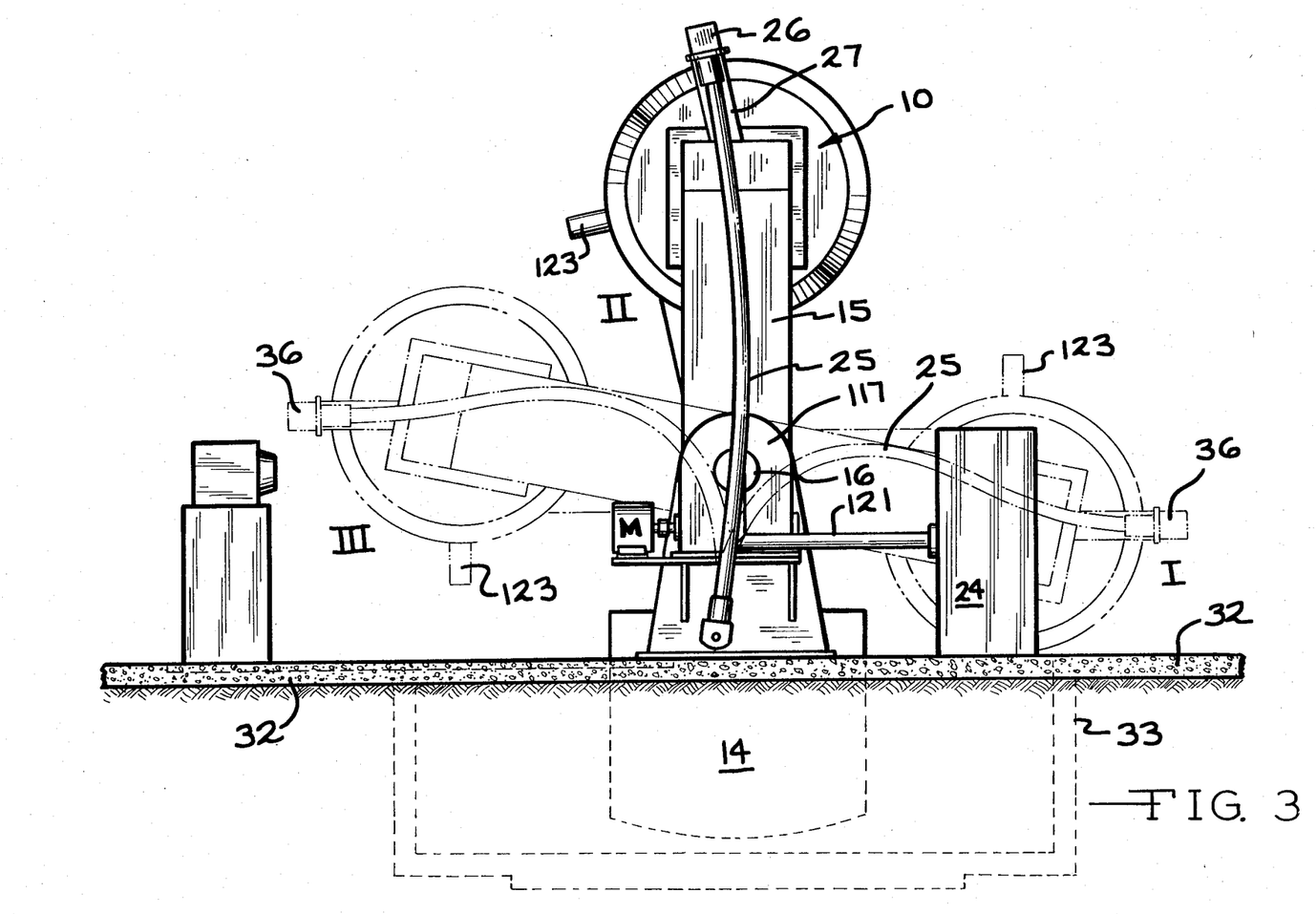
FIG. 3 is a right end view of the cyclotron of FIG. 1 particularly illustrating the variable positioning of a liquified gas flexible hose (25) as a result of different positioning of the cyclotron.

As shown in FIG. 1, the patient P is provided on a table 35 with a flat surfaced fixed top 36 and horizontally slideable top 36a supporting the patient P and with legs 37 which are vertically adjustable from pad 32. Beneath the table 37 a first x-ray unit 38 is provided with a beam 39 vertically focussed towards the back of patient P. As shown in FIG. 2 a second x-ray unit 40 with a horizontally focussed beam 41 towards the side of the patient P is also provided. The second x-ray unit 40 is moveable on a track 42 (shown in broken lines) to provide an approach to the side of the patient P on the table 35 and to provide for removal when the cyclotron 10 is in position III of FIG. 2.

CYCLOTRON

The construction and operation of the superconducting cyclotron 10 is known and requires only a brief description. A similar higher MeV fixed support cyclotron is operating at Michigan State University, East Lansing, Mich.

Figure 4:
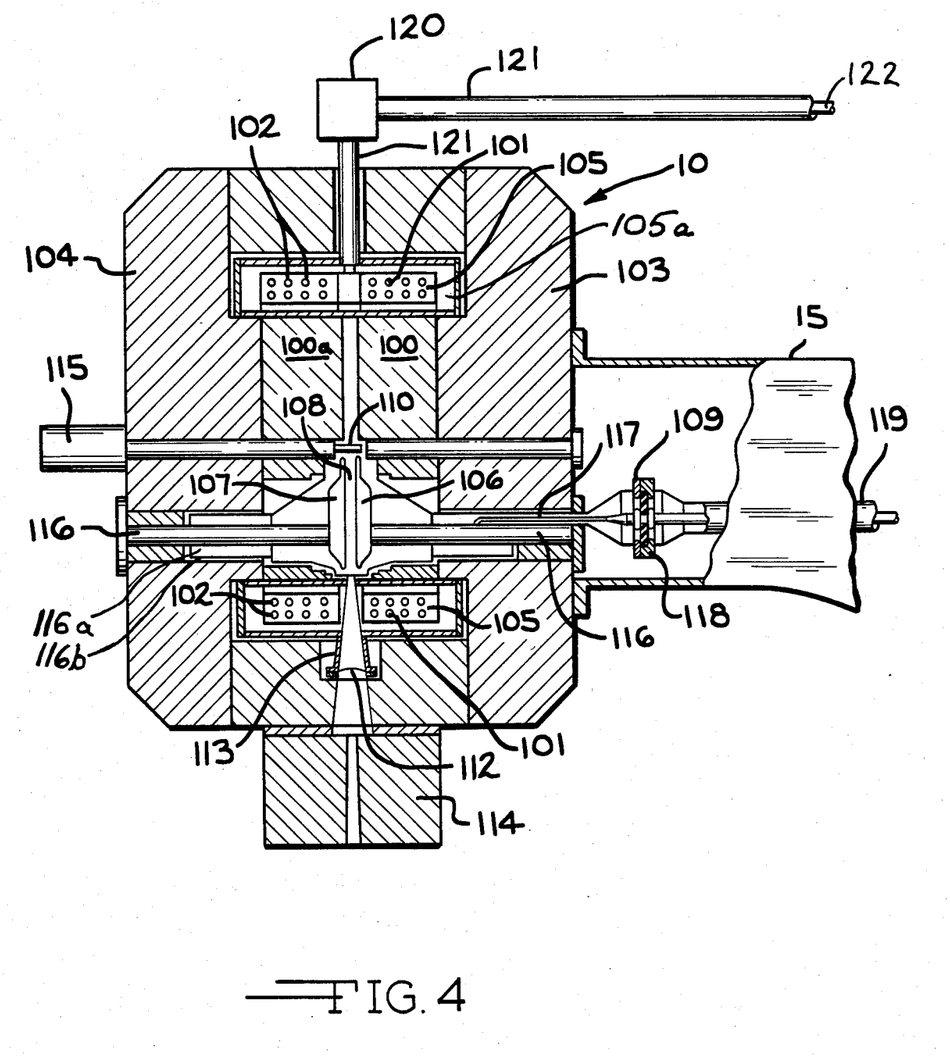
FIG. 4 is a front cross-sectional view of the cyclotron shown in FIG. 1.
Figure 5:
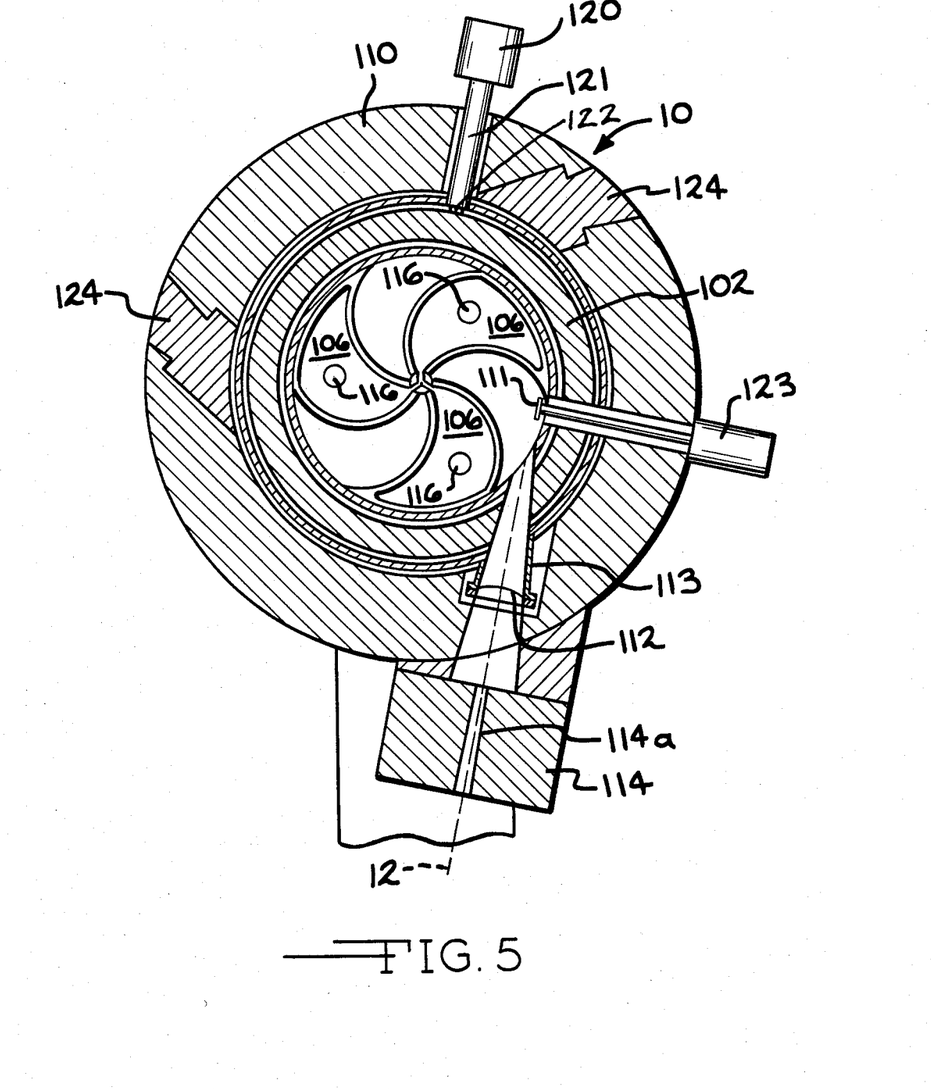
FIG. 5 is a left end cross-sectional view of the cyclotron shown in FIG. 1.

Referring to FIGS. 4 and 5, the cyclotron 10 has large iron poles 100 and 100a with superconducting coils 101 and 102 vertically oriented around the poles 100 and 100a and with iron frames 103 and 104 defining a magnetic field return loop. The coils 101 and 102 are cooled with a liquified gas at near 0° K., such as by liquid helium, in a helium vessel 105. This renders the coils 101 and 102 superconductive and thus reduces the weight of the cyclotron per MeV. A vacuum wall 105a is provided around vessel 105 for insulation.

Positive ion acceleration is achieved with three identical spaced apart pairs of electrodes or dees 106, 107 defining a gap 108 in a vacuum chamber. The dees 106 and 107 are connected to a high-frequency, high-voltage oscillator circuit 24 through coaxial transmission line 119, feed through insulator 118, feed through insulator housing 109, and coupling loop 117 which joins the dee stem 116. The dee stems 116 are the inner conductor of a quarter wave transmission line, the electrical length of which is determined by the position of the clamped but adjustable short circuit connection 116a between the inner conductor not which is the dee stem 116 and the outer conductor 116b of the dee stem 116 transmission line 116 and 116b, this electrical length being adjusted so that the complete dee 106 and 107 and dee stem 116 system has a natural resonance at a frequency which provides acceleration of the atomic particles. The rapidly alternating RF field is provided across each of the dees 106 and 107 by the circuit 24 and coaxial transmission line 119.

Positive ions are provided by an ion source 110 at the center of the evacuated vacuum chamber 108. The magnetic field between poles 100 and 100a is perpendicular to the dees 106 and 107. The electrical field between the dees 106 and 107 and the tips of adjacent poles 100 and 100a is phased such that the ion is accelerated by each dee assembly 106 and 107 in succession as it leaves the ion source 110. The magnetic field forces the ion into a circular path. The magnetic field is proportioned and the electric field between the dees 106 and 107 and the adjacent pole tips 100 and 100a is phased such that the ion from the ion source is accelerated by each dee assembly 106 and 107 in succession, as it passes in the multiturn spiral orbit from ion source to the target 111 in a helical coil. The ion hits a target 111 tangentially to produce neutrons 12 which escape through a window 112 housed in a holder 113 through a collimator 114 as a beam 12.

The advantage of a superconducting cyclotron 10 is that it is smaller than early types which were only water cooled and thus are less practical for the present application. The total weight of the present unit is about 14 tons.

Other elements in the cyclotron include: (1) an ion source vacuum lock 115; (2) electrical connector stems 116 for dees 106 and 107, RF coupling loop 117, RF feed through insulator 118 and RF coaxial transmission line 119; (3) liquified gas inlet from conduit 122 and vent space or annular conduit 121 adjacent the support box 120; (4) non-magnetic inserts 124 which cancel the magnetic perturbation of the exit pipe 113 and window 112 hole in the magnet outer yoke 104a; (5) vapor cooled electrical leads for the superconducting coils 101 and 102 (not shown—available from American Magnetics Corporation, Oak Ridge, Tenn.) which mount in the inlet box 120 and provide for the connection of electrical cables (not shown) to the low temperature superconducting coils 101 and 102.

In the operation of the cyclotron 10, positively charged proton particles or other positively charged atomic particles are accelerated in a helical path between dees 106 and 107 so as to hit the target 111 tangentially to release neutrons which pass through exit window 112 and through opening 114a of collimator 114 as a beam 12 which is directed at the target or patient P. The target 111 is preferably beryllium. The protons hitting the target are at between about 25 to 75 MeV, and for medical purposes preferably about 50 MeV. The neutrons produced are between about 1 to 50 MeV. The cyclotron can use about 5 liters per hour of liquid helium which can be vented or returned to the source of supply (not shown). As can be seen, the present invention provides reliable and more versatile support structure for a cyclotron.

We claim:

1. A superconducting cyclotron (10) apparatus including ion source means (110) for providing charged atomic particles to be spirally accelerated in the cyclotron with superconducting coils (101, 102) around iron magnetic poles (110, 100a) and which can be cooled with a liquified gas to near 0° K., RF generator means (24) connected (119) to dees (106, 107) for spirally accelerating the charged atomic particles to generate a beam of particles or sub-particles from the spirally accelerated charged particles, the cyclotron including a support structure (11) rotatable around a pivot axis (A—A) for the cyclotron and balanced around the pivot axis by a counterweight (14) on the support structure to thereby change the angle of the beam wherein the beam can be directed towards the axis in an arc defining a plane of rotation of the cyclotron by the support structure, the improvement in the support structure which comprises:
   (a) a balance bar (13) with two ends including a counterweight (14) at one end of the balance bar opposite a pivot axis (A—A) and a cross bar (15) member at the other end opposite the counterweight, perpendicular to the balance bar and parallel to the pivot axis for supporting the cyclotron mounted on one end of the cross bar such that the beam can be generated in a plane perpendicular to and in the direction of the pivot axis;
   (b) pivot means (16, 17) supporting the balance bar at the pivot axis of the balance bar with the cyclotron and cross bar balancing the counterweight and with the pivot axis providing a fulcrum such that the balance bar is rotatable in an arc of about 180° in the plane perpendicular to the pivot axis;
   (c) drive means (18) for rotating the balance bar in the arc as the beam is generated; and
   (d) flexible hose (25) attached at one end to the cross bar at an opposite end from the cyclotron for providing a liquified gas (34) cooled to near 0° K. through the hose to the cyclotron through an inlet conduit (122) supported by the cross bar with an opposite end (31) of the hose attached to a fixed base (32) providing a mounting surface (B—B) for the support structure wherein as the cyclotron is moved in the arc the hose bends between the base and cross bar.

2. The apparatus of claim 1 wherein the pivot means is a pivot pin mounted around the pivot axis of the balance bar and wherein holders on the mounting surface support the pin for rotation of the balance bar.

3. The apparatus of claim 2 wherein a circular gear (19) is mounted on an extended end of the pivot pin and wherein a worm gear (20) driven by a motor (m) is mated to the circular gear for rotation of the pin and balance bar.

4. The apparatus of claim 3 wherein the RF generating means (24) is connected through a rotary RF joint (23) and through the pivot pin and inside the balance bar and cross bar to the cyclotron dees.

5. The apparatus of claim 2 wherein the holders are mounted on a concrete pad as the fixed base.

6. The apparatus of claim 1 wherein the counterweight is positioned in an opening (33) in and below the mounting surface of the fixed base.

7. The apparatus of claim 1 wherein a table (35) with legs (37) for vertically and horizontally adjusting a positioning surface for a horizontal patient (P) is mounted above the mounting surface such that selected points of the patient are bombarded with the beam.

8. The apparatus of claim 7 wherein an x-ray unit (40, 41) is moveable on a track (42) across the mounting surface of the fixed base so as to be adjacent the table positioning surface.

9. The apparatus of claim 1 wherein the cyclotron has a vent space in an annular conduit (121) around the inlet conduit and wherein the coils are adapted to be cooled with liquified gas filling up to approximately half of the vessel such that as the cyclotron is rotated in the arc the liquified gas is below the inlet means and is thereby prevented from draining from the cyclotron through the vent space.

10. The apparatus of claim 9 wherein the arc of the cyclotron is less than about 180°.

11. In a superconducting cyclotron (10) apparatus which generates a beam of high velocity atomic particles or subparticles (12) around and above an object to be irradiated from spirally accelerated charged atomic particles which impinge upon a target (111) to produce the beam, with a window (112) and a collimator (114) on a first side of the cyclotron tangential to the spirally accelerated charged atomic particles for defining the beam (12), including a support structure (11) having a counterweight (14) for the cyclotron rotatable on a pivot axis (A—A) between the cyclotron and counterweight (14) for changing the angle of the beam in an arc of 180° defining a plane around the axis so that an object beneath the cyclotron can be irradiated around the axis the improvement in the cyclotron which comprises:

inlet means (122) for supplying liquified gas to a vessel (150) with a vent space (121) from the vessel for releasing liquified gas which becomes a gas in operation of the cyclotron adjacent the inlet means and with superconducting coils (101, 102) in the vessel vertically wound around spaced apart iron poles (100, 100a) which can generate a magnetic field between the poles and which functions to produce the spirally accelerated charged atomic particles with an oscillating electrical field, wherein the inlet means is mounted on a second side of the cyclotron opposite the window and collimator, wherein in use the liquified gas supplied by the inlet means fills up to approximately one-half of the vessel and partially covers each of the coils so that the coils are superconducting such that as the cyclotron is rotated in the arc, the liquified gas is below the inlet means and is thereby prevented from draining from the cyclotron through the vent space.

12. The apparatus of claim 11 wherein the cyclotron is mounted on one end of a cross bar (15) and liquified gas supply means on an opposite end of the cross bar with a first end of a balance bar (13) intermediate the cross bar ends such that the cross bar and balance bar form a T, wherein the balance bar is provided with a counterweight (14) on a second end opposite the first end and wherein bearing members (16, 17) are provided intermediate the first and second balance bar ends mounted on the pivot axis so as to provide a balanced fulcrum between the counterweight and the cyclotron and cross bar.

13. The apparatus of claim 12 wherein flexible hoses (25 and 29) and flexible electrical cables (28) are mounted at the end of the cross bar opposite the cyclotron, wherein one of the hoses provides liquified gas to a rigid conduit supported by the support bar through the inlet means to the cyclotron and the remaining hoses provide another cooling liquid to the cyclotron and wherein the flexible electrical cables provide power to the cyclotron through rigidly mounted electrical supply cables supported by the cross bar.

14. The apparatus of claim 13 wherein the bearing members for the balance bar are mounted on a fixed base (32) providing a mounting surface (B—B) and wherein the flexible hoses and cables are rigidly supported on the mounting surface so as to bend when the cyclotron and cross bar are rotated by the balance bar.

15. The method of using a superconducting cyclotron (10) apparatus which generates a beam of high velocity particles or sub-particles from spirally accelerated charged particles which impinge upon a target to produce the beam with a window (112) and collimator (114) on a first side of the cyclotron tangential to the spirally accelerated charged particles for defining the beam (12), including a support structure (11) for the cyclotron rotatable on a pivot axis in an arc of about 180° or less for changing the angle of the beam in an arc defining a plane around the axis so that an object beneath the cyclotron can be irradiated by the beam around the axis which comprises:

(a) providing an object (P) to be irradiated such that the beam of high velocity particles irradiates the object as the cyclotron is rotated on the pivot axis;

(b) supplying a liquified gas (34) at near 0° K. in the cyclotron through an inlet means (122) to a vessel (105) containing vertically oriented superconducting coils (101, 102) around iron poles for generating a magnetic field in the cyclotron which functions to produce the spirally accelerated charged particles with an oscillating electrical field with a vent space (121) for releasing boiled off liquified gas which becomes a gas during operation of the cyclotron adjacent the inlet means, wherein the inlet means is on a side of the cyclotron opposite the collimator and wherein the liquified gas fills up to approximately half of the vessel and partially covers each of the coils so that the coils are superconducting, such that when the cyclotron is rotated in the arc the liquified gas which remains in the vessel is below the inlet means and is thereby prevented from draining from the cyclotron through the vent space; and (c) irradiating the object with the beam as the cyclotron is rotated in the arc.

16. The method of claim 15 wherein the object is an animal.

17. The method of claim 16 wherein the animal is human.

* * * * *